United States Patent
Zheng et al.

(10) Patent No.: US 10,411,301 B2
(45) Date of Patent: Sep. 10, 2019

(54) IONIC LIQUIDS AND PREPARATION METHOD THEREOF

(71) Applicant: Microvast Power Systems Co., Ltd., Huzhou, Zhejiang Province (CN)

(72) Inventors: Zhuoqun Zheng, Huzhou (CN); Dawei Shen, Huzhou (CN); Zhenyu Fei, Huzhou (CN)

(73) Assignee: MICROVAST POWER SYSTEMS CO., LTD., Huzhou, Zhejiang Province (CN)

( * ) Notice: Subject to any disclaimer, the term of this patent is extended or adjusted under 35 U.S.C. 154(b) by 175 days.

(21) Appl. No.: 15/413,396

(22) Filed: Jan. 23, 2017

(65) Prior Publication Data

US 2017/0222266 A1 Aug. 3, 2017

(30) Foreign Application Priority Data

Feb. 2, 2016 (CN) .......................... 2016 1 0072969

(51) Int. Cl.
| | |
|---|---|
| *H01M 4/02* | (2006.01) |
| *H01M 10/0568* | (2010.01) |
| *C07C 211/63* | (2006.01) |
| *C07D 207/06* | (2006.01) |
| *C07D 207/20* | (2006.01) |
| *C07D 295/037* | (2006.01) |
| *H01M 10/0525* | (2010.01) |
| *C07C 311/09* | (2006.01) |
| *H01M 10/0569* | (2010.01) |

(52) U.S. Cl.
CPC ....... *H01M 10/0568* (2013.01); *C07C 211/63* (2013.01); *C07C 311/09* (2013.01); *C07D 207/06* (2013.01); *C07D 207/20* (2013.01); *C07D 295/037* (2013.01); *H01M 10/0525* (2013.01); *H01M 10/0569* (2013.01); *H01M 2300/0028* (2013.01)

(58) Field of Classification Search
CPC ...................................................... H01M 4/02
See application file for complete search history.

(56) References Cited

U.S. PATENT DOCUMENTS 4,892,944 A * 1/1990 Mori .................. C07D 295/023
544/107

FOREIGN PATENT DOCUMENTS

| CN | 1854129 A | 11/2006 |
|---|---|---|
| CN | 101245019 A | 8/2008 |
| CN | 101516829 A | 8/2009 |
| CN | 102199096 A | 9/2011 |
| CN | 105209432 A | 12/2015 |

OTHER PUBLICATIONS

Zhenquan Zhang, Jigeng Tang, Liankui Gao, Guoxiang Jia, "Salification", Chinese Journal of Organic Chemistry, Sep. 1989, p. 268, Issue 1, Northeast Normal University Press Publisher, Changchun, China.

* cited by examiner

*Primary Examiner* — Jacob B Marks
(74) *Attorney, Agent, or Firm* — Cheng-Ju Chiang

(57) ABSTRACT

The present disclosure provides an ionic liquid and a preparation method thereof, in particular, the present disclosure provides an ionic liquid whose halogen anions content and moisture content are low, and a method for preparing the same. The total content of halogen anions in the ionic liquid is less than 10 ppm, and moisture content in the ionic liquid is less than 50 ppm. The ionic liquid prepared by the method of the present disclosure is suitable for electrochemical systems which have high requirements for moisture content, such as lithium ion secondary batteries and electrochemical supercapacitors.

22 Claims, No Drawings

IONIC LIQUIDS AND PREPARATION METHOD THEREOF

CROSS REFERENCE TO RELATED APPLICATION

The present application is based on and claims priority of Chinese patent application No. 201610072969.9, filed on Feb. 2, 2016. The entire disclosure of the above-identified application, including the specification, drawings and claims are incorporated herein by reference in its entirety.

FIELD OF THE INVENTION

The present disclosure relates to ionic liquids and the preparation method thereof, particularly to ionic liquids which has low halogen ion content and low water content.

BACKGROUND OF THE INVENTION

An ionic liquid is a liquid material which is entirely composed of ions. Because the ionic liquid remains liquid at room temperature or at a lower temperature (from −97° C. to 100° C.), it is described as a room temperature molten salt or a low temperature molten salt, and also as a liquid organic salt. There are many types of ionic liquids, and according to different organic cations, ionic liquids can be divided into quaternary ammonium salts, quaternary phosphonium salts, nitrogen heterocyclic onium salts etc., wherein the nitrogen heterocyclic type ionic liquids include imidazolium onium salts, pyridinium onium salts, piperidinium salts, pyrrolidine salts etc. In addition, there are various types of anions which could constitute ionic liquids, wherein inorganic anions comprise $F^-$, $Cl^-$, $Br^-$, $I^-$, $NO_3^-$, $CO_3^{2-}$, $PF_6^-$, $BF_4^-$, $C_2O_4^{2-}$, $SO_4^{2-}$, $PO_4^{3-}$, $Al_2Cl_7^-$ etc., while organic anions comprise $CH_3COO^-$, $CF_3SO_3^-$, $C_4H_9SO_3^-$, $CF_3COO^-$, $N(CF_3SO_2)_2^-$, $N(C_2F_5SO_2)_2^-$, $N(C_4F_9SO_2)_2^-$, $N[(CF_3SO_2)(C_4F_9SO_2)]^-$, $C(CF_3SO_2)_3^-$, etc. Theoretically speaking, there are more than $10^{18}$ kinds of ionic liquids. Structures of cations and anions of several common ionic liquids are as follows:

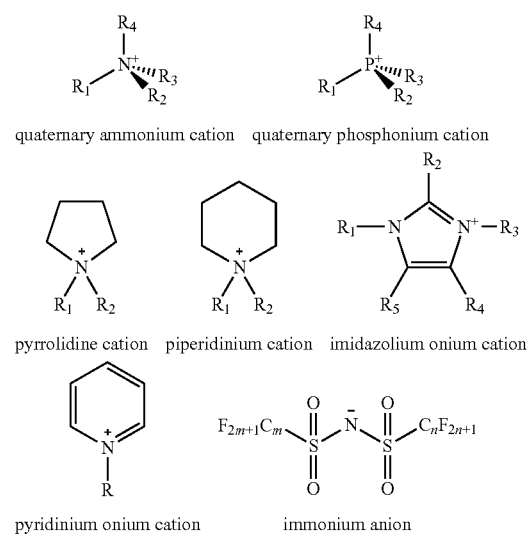

quaternary ammonium cation   quaternary phosphonium cation pyrrolidine cation   piperidinium cation   imidazolium onium cation pyridinium onium cation   immonium anion Recently, extensive research has been conducted on applying ionic liquids into electrolytes of electrochemical power sources, and research of applying ionic liquids as electrolytes of lithium battery systems has been an important branch of electrochemical fields. Electrolyte purity in electrochemical power sources especially in lithium battery systems is strictly required. Generally, content of halogen ions ($Cl^-$, $Br^-$, $I^-$) in electrolytes is under 15 ppm, and that of water in electrolytes is under 80 ppm. If halogen ion residues exist in ionic liquid electrolyte, they will have great influence on the application of ionic liquid electrolyte in secondary batteries. Such halogen ions can corrode battery cases, current collectors, and tabs etc., which will badly affect the charge-discharge efficiency and cycle life of batteries. In addition, if water exists in ionic liquid electrolytes, it will react with lithium electrolyte salts, solvents and active electrode materials, which may lead to battery flatulence or bulge phenomenon etc. In view of the above, in order to yield an ionic liquid with lower halogen ion content, it is necessary to provide a synthesis method whose alkylating agent is not halogenated hydrocarbons. However, taking quaternary ammonium salts as an example, it is conventionally prepared by a reaction between tertiary amines and halogenated hydrocarbons. Such method can only prepare quaternary ammonium salts whose anions are $Cl^-$, $Br^-$, or $I^-$, other quaternary ammonium salts with anions other than $Cl^-$, $Br^-$ and $I^-$ can only be prepared by an ion exchange reaction. However, such ion exchange reaction will inevitably bring halogen ion residues.

U.S. Pat. No. 4,892,944 describes a method of preparing quaternary ammonium/phosphonium salts using dimethyl carbonate as an alkylating agent. The method includes two steps, in the first step, tertiary amine/phosphine reacts with dimethyl carbonate to generate a quaternary ammonium/phosphonium methyl carbonate; in the second step, the quaternary ammonium/phosphonium methyl carbonate reacts with an acid to release methanol and carbon dioxide, and yields a quaternary ammonium/phosphonium salt. The anion species of the quaternary ammonium/phosphonium salts are determined by the acids used in the second step. The reaction equations are as follows:

$$R_1R_2R_3N(P) + Me_2CO_3 \rightarrow [R_1R_2R_3N(P)Me]^+MeCO_3^- \quad (1)$$

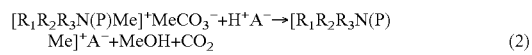

$$[R_1R_2R_3N(P)Me]^+MeCO_3^- + H^+A^- \rightarrow [R_1R_2R_3N(P)Me]^+A^- + MeOH + CO_2 \quad (2)$$

No ion exchange reaction is needed in the method above, in this way, halogen ion residues can be avoided, and the anions of the yielded quaternary ammonium/phosphonium salts derive from anions of various acids. However, in the second step of the method above, when certain anions are introduced by adding acids whose acidity is stronger than that of carbonic acids, moisture will be inevitably brought into final products. For example, in order to yield an ionic liquid whose anion is $BF_4^-$, $HBF_4$ aqueous solution is added, thereby water is introduced. Most of the water can be removed by methods of washing, recrystallization or drying, but some moisture residues will remain and it is difficult to be removed completely.

Chinese Patent No. 200610091637.1 discloses an ionic liquid whose content of alkali metal impurity is under 5 ppm while that of the halogen ions is under 1 ppm, and it also discloses a method to synthesize quaternary ammonium/phosphonium salts via acids or esters. However, the anions of the ionic liquids are merely limited to halogenated sulfonyl imide ions. Further, the synthesis process has no moisture control, particularly, the specification describes that water is a preferable solvent, therefore there is no limitation to the content of water in the ionic liquid.

Chinese Patent No. 200710008626.7 discloses a process wherein a dialkyl carbonate reacts with an amine (ammonium) salt at a suitable temperature and a pressure (50° C.~300° C., 0.5 MPa~50 MPa, 4~12 hours) to generate a quaternary ammonium salt. Such process takes the carbonate ester as an alkylating agent, and the hydrogen of the amine salt is substituted by methyl in reaction and thus the quaternary ammonium salt is obtained. The reaction equation is as below:

$$[R_1R_2R_3NH]^+ + Me_2CO_3 \rightarrow [R_1R_2R_3NMe]^+ + MeOH + CO_2 \qquad (3)$$

The process above has no residues of halogen anions. Though such process emphasizes on the synthesis of corresponding quaternary ammonium salt from an amine/ammonium salt, it provides no special synthesis method of such anime/ammonium salt. According to the description of the specification, it takes the products yielded from a neutralization reaction between an amine/ammonia and an acid as reactants, such as $NH4^+L^-$, $RNH_3^+L^-$, $R_1R_2NH_2^+L^-$, $R_1R_2R_3NH^+L^-$. However, most of the inorganic acids contain water, and as a result moisture will be inevitably introduced during the synthesis of the amine/ammonium salt. Therefore, such problem is still unsolved in the patent, that is, how to synthesis an ionic liquid which has low moisture content.

SUMMARY OF THE INVENTION

In order to solve the problems above, the present disclosure provides an ionic liquid, wherein total content of the halogen anions in such ionic liquid is less than 10 ppm, moisture content in such ionic liquid is less than 50 ppm. In one embodiment, the total content of the halogen anions in the ionic liquid is less than 5 ppm, and the moisture content in the ionic liquid is less than 50 ppm. The halogen anions refer to $Cl^-$, $Br^-$ and $I^-$.

In conventional method which includes the following steps, first substituted by alkyl halides and then conducting an ion exchange process, in the ionic liquid yielded by such method, the content of the halogen ions (even after a purification treatment) is generally over 10 ppm, and moisture content is generally over 50 ppm. In addition, if the moisture content of the ionic liquid is higher than 100 ppm or the content of the halogen ions is higher than 30 ppm, the life-span of the batteries will be obviously decreased, followed by battery swollen etc. In contrast, in the present disclosure, in the yielded ionic liquids, the content of the halogen anions can be less than 10 ppm, and the moisture content can be less than 50 ppm. In one embodiment, the content of the halogen anions is less than 5 ppm, and the moisture content is less than 50 ppm. In the present disclosure, the halogen anions only refer to $Cl^-$, $Br^-$ and $I^-$. Therefore, in the present disclosure, the total content of the halogen anions also refer to that of the three anions $Cl^-$, $Br^-$ and $I^-$ in the ionic liquid.

In one embodiment, the cation of the ionic liquids is at least one selected from the following structures:

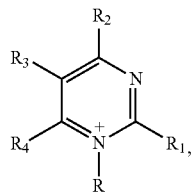
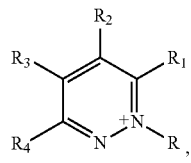

-continued

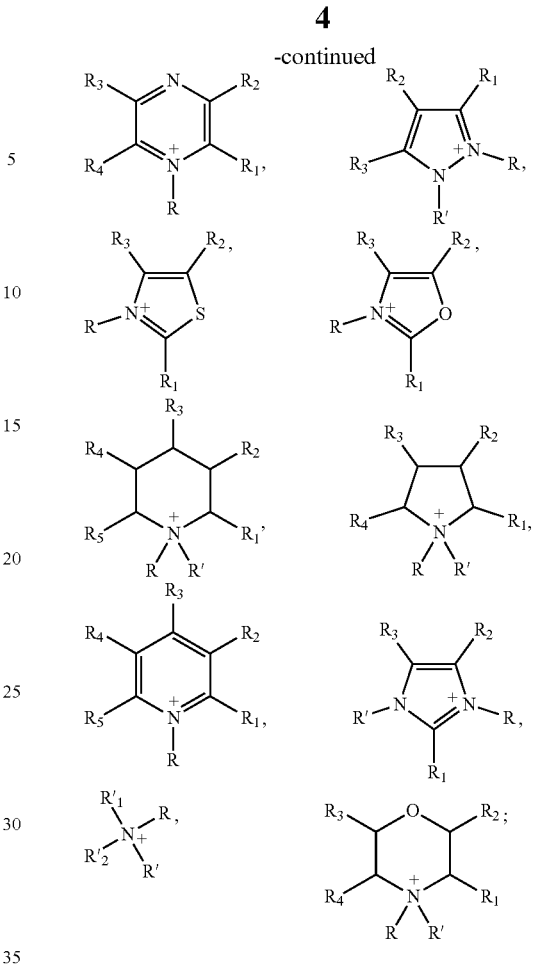

Wherein each of said R, R', $R'_1$ and $R'_2$ is separately selected from alkyl, alkenyl, alkynyl, phenyl or aryl; or said R, R', $R'_1$ and $R'_2$ is an organic group including at least one element selected from boron, silicon, nitrogen, phosphorus, oxygen, sulfur, fluorine, chlorine, bromine and iodine; in one embodiment, the described organic group is alkyl, alkenyl, alkynyl, phenyl or aryl. In one embodiment, each of the R, R', $R'_1$ and $R'_2$ is an independent substituent group; or at least two of the R, R', $R'_1$ and $R'_2$ adjacent to each other joint into a ring.

Wherein, each of said $R_1$, $R_2$, $R_3$, $R_4$ and $R_5$ is selected from hydrogen, alkyl, alkenyl, alkynyl, phenyl or aryl; or each of said $R_1$, $R_2$, $R_3$, $R_4$ and $R_5$ is a group including at least one element selected from the following: boron, silicon, nitrogen, phosphorus, oxygen, sulfur, fluorine, chlorine, bromine and iodine; each of said R, R', $R_1$, $R_2$, $R_3$, $R_4$, $R_5$, $R'_1$, $R'_2$ is an independent substituent group; or at least two of said R, R', $R_1$, $R_2$, $R_3$, $R_4$, $R_5$, $R_6$, $R'_1$, $R'_2$ adjacent to each other joint into a ring.

In one embodiment, each of said $R_1$, $R_2$, $R_3$, $R_4$ and $R_5$ in the present disclosure is an organic group including at least one element selected from the following: boron, silicon, nitrogen, phosphorus, oxygen, sulfur, fluorine, chlorine, bromine and iodine, wherein the organic group is alkyl, alkenyl, alkynyl, phenyl or aryl. In another embodiment, each of said $R_1$, $R_2$, $R_3$, $R_4$ and $R_5$ is at least one selected from fluorine, chlorine, bromine and iodine.

In one embodiment, the anion of the ionic liquids is at least one selected from the following: $PF_6^-$, $BF_4^-$, $SO_4^{2-}$, $NO_3^-$, $F^-$, $PO_4^{3-}$, $ClO_4^-$, $SiF_6^{2-}$, $CH_3CO_2^-$, $CF_3CO_2^-$, $C_3F_7CO_2^-$, $(CN)_2N^-$.

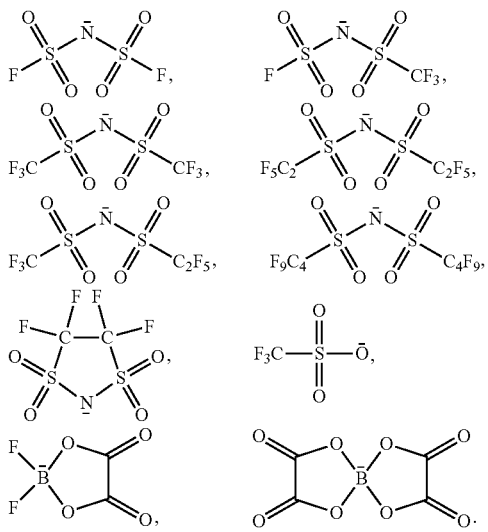

The present disclosure also provides a method for preparing the ionic liquid, which includes the following steps:

Step 1: preparing an ammonium salt or a phosphonium salt with the following reactions:

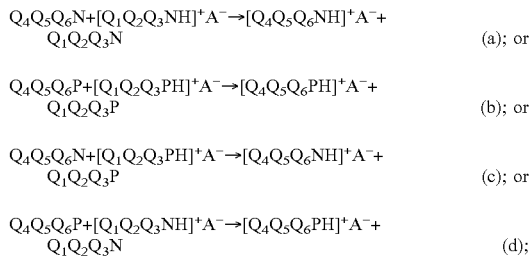

Step 2: The ammonium salt or the phosphonium salt prepared in step 1 react with a carbonate ester to produce a quaternary ammonium salt or a quaternary phosphonium salt, the reaction equations are as follows,

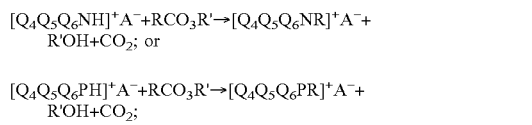

Wherein each of $Q_4$, $Q_5$, $Q_6$, $Q_1$, $Q_2$ and $Q_3$ is selected from hydrogen, alkyl, alkenyl, alkynyl, phenyl or aryl; or each of $Q_4$, $Q_5$, $Q_6$, $Q_1$, $Q_2$ and $Q_3$ is an organic group including at least one element selected from boron, silicon, nitrogen, phosphorus, oxygen, sulfur, fluorine, chlorine, bromine and iodine. In one embodiment, the organic group is alkyl, alkenyl, alkynyl, phenyl or aryl; in another embodiment, $Q_4$, $Q_5$, $Q_6$, $Q_1$, $Q_2$ and $Q_3$ adjacent to each other joint into a ring; in yet another embodiment, the organic group is alkyl, alkenyl, alkynyl, phenyl or aryl.

Wherein each of R and R' is selected from alkyl, alkenyl, alkynyl, phenyl or aryl; or each of R and R' is a group including at least one element selected from boron, silicon, nitrogen, phosphorus, oxygen, sulfur, fluorine, chlorine, bromine or iodine. In one embodiment, each of the R and R' is an independent substituent group. In another embodiment, the R and R' adjacent to each other joint into a ring.

Wherein the R or R' in the present disclosure is separately a group including at least one element selected from the following: boron, silicon, nitrogen, phosphorus, oxygen, sulfur, fluorine, chlorine, bromine and iodine. In another embodiment, the R or R' is separately an organic group including at least one element selected from the following: boron, silicon, nitrogen, phosphorus, oxygen, sulfur, fluorine, chlorine, bromine and iodine. In yet another embodiment, the organic group is alkyl, alkenyl, alkynyl, phenyl or aryl. In still another embodiment, R or R' is separately selected from at least one of the following: fluorine, chlorine, bromine and iodine.

In one embodiment, in step 1, alkalinity of the $Q_4Q_5Q_6N$ in reaction equation (a) is stronger than that of $Q_1Q_2Q_3N$. In one embodiment, in step 1, $Q_1Q_2Q_3N$ is a volatile gas and $Q_4Q_5Q_6N$ is a liquid or a solid whose boiling point is higher than that of $Q_1Q_2Q_3N$.

In one embodiment, $Q_1Q_2Q_3N$ in reaction equation (a) of step 1 is a volatile gas; and $Q_4Q_5Q_6N$ is a liquid or a solid whose volatility is lower than that of $Q_1Q_2Q_3N$ and boiling point is higher than that of $Q_1Q_2Q_3N$.

In one embodiment, alkalinity of $Q_4Q_5Q_6P$ in reaction equation (b) of step 1 is stronger than that of $Q_1Q_2Q_3P$; or $Q_1Q_2Q_3P$ is a volatile gas and $Q_4Q_5Q_6P$ is a liquid or a solid whose boiling point is higher than that of $Q_1Q_2Q_3P$.

In one embodiment, $Q_1Q_2Q_3P$ in reaction equation (b) of step 1 is a volatile gas and $Q_4Q_5Q_6P$ is a liquid or a solid whose boiling point is higher than that of $Q_1Q_2Q_3P$. In another embodiment, $Q_1Q_2Q_3P$ in reaction equation (b) of step 1 is a volatile gas, and $Q_4Q_5Q_6P$ is a liquid or a solid whose volatility is lower than that of $Q_1Q_2Q_3P$ and boiling point is higher than that of $Q_1Q_2Q_3P$.

In one embodiment, alkalinity of $Q_4Q_5Q_6N$ in reaction equation (c) of step 1 is stronger than that of $Q_1Q_2Q_3P$; or $Q_1Q_2Q_3P$ is a volatile gas and $Q_4Q_5Q_6N$ is a liquid or a solid whose boiling point is higher than that of $Q_1Q_2Q_3P$.

In one embodiment, $Q_1Q_2Q_3P$ in reaction equation (c) of step 1 is a volatile gas and $Q_4Q_5Q_6N$ is a liquid or a solid whose boiling point is higher than that of $Q_1Q_2Q_3P$. In another embodiment, $Q_1Q_2Q_3P$ in reaction equation (c) of step 1 is a volatile gas, and $Q_4Q_5Q_6N$ is a liquid or a solid whose volatility is lower than that of $Q_1Q_2Q_3P$ and boiling point is higher than that of $Q_1Q_2Q_3P$.

In one embodiment, alkalinity of $Q_4Q_5Q_6P$ in reaction equation (d) of step 1 is stronger than that of $Q_1Q_2Q_3N$; or $Q_1Q_2Q_3N$ is a volatile gas and $Q_4Q_5Q_6P$ is a liquid or a solid whose boiling point is higher than that of $Q_1Q_2Q_3N$.

In one embodiment, $Q_4Q_5Q_6N$ in reaction equation (d) of step 1 is a volatile gas and $Q_4Q_5Q_6P$ is a liquid or a solid whose boiling point is higher than that of $Q_1Q_2Q_3N$. In another embodiment, $Q_1Q_2Q_3N$ in reaction equation (d) of step 1 is a volatile gas, and $Q_4Q_5Q_6P$ is a liquid or a solid whose volatility is lower than that of $Q_1Q_2Q_3N$ and boiling point is higher than that of $Q_1Q_2Q_3N$.

As described above, step 1 of the present disclosure provides a method to synthesize an ammonium salt or a phosphonium salt whose content of halogen anions (Cl—, Br—, I—) is less than 10 ppm and moisture content is less than 50 ppm. The synthesis is based on principles of 'preparing weak alkalis by strong alkalis' or 'preparing volatile alkalis by non-volatile alkalis'. In one embodiment, step 1 provides a method to synthesize an ammonium salt or a phosphonium salt whose content of halogen anions (Cl$^-$, Br$^-$, I$^-$) is less than 5 ppm and whose moisture content is less than 50 ppm. Taking nitrogenous compounds as an example, such nitrogenous compounds are sp$^3$-hybridized ammonias or amines, or sp2-hybridized imine derivatives.

For example, since the alkalinity of tributylamine is stronger than that of ammonia or trimethylamine, fluorinated tributyl ammonium salt ($[(C_4H_9)_3NH]^+F^-$) can be prepared by the reaction between tributylamine and fluorinated trimethyl ammonium salt ([(CH$_3$)$_3$NH]$^+$F$^-$), as below:

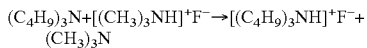

For another instance, in the reaction below, since ammonia (NH$_3$) is a volatile alkali, fluorinated propyl piperidinium salt can be prepared by the reaction between N-propyl piperidine and ammonium fluoride (NH$_4$F):

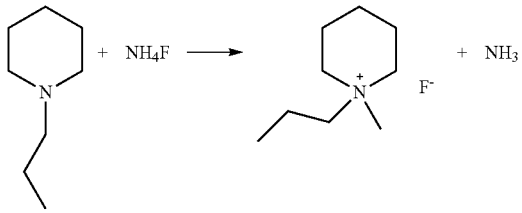

The fluorinated trimethyl ammonium salt ([(CH$_3$)$_3$NH]$^+$F$^-$) can be prepared by the reaction between dry trimethylamine gas and HF gas. Anhydrous products can be obtained if the process condition is properly controlled. Similarly, anhydrous ammonium fluoride (NH$_4$F) can be prepared by dry NH$_3$ gas and dry HF gas. There is no limitation on how to prepare anhydrous or low moisture content amine salts or ammonium salts in the present disclosure. The feed reactants and solvents have been subject to a previous water removal treatment by methods of distillation or molecular sieve adsorption, in order to ensure the moisture content less than 50 ppm. Further, dry inert gas protection can be applied during the reaction in order to ensure the air tightness of the reactor.

In step 1, the preparation of amine salts or phosphonium salts can also be realized by the following reactions:

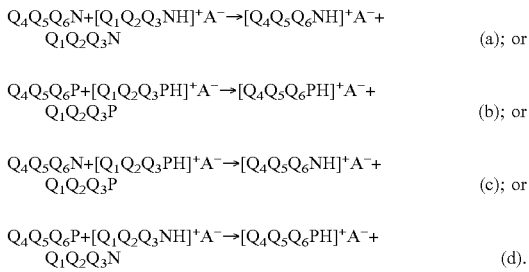

Wherein each of said Q$_4$, Q$_5$, Q$_6$, Q$_1$, Q$_2$ and Q$_3$ is selected from hydrogen, alkyl, alkenyl, alkynyl, phenyl or aryl; or each of Q$_4$, Q$_5$, Q$_6$, Q$_1$, Q$_2$ and Q$_3$ is an organic group including at least one element selected from boron, silicon, nitrogen, phosphorus, oxygen, sulfur, fluorine, chlorine, bromine and iodine; The organic group is alkyl, alkenyl, alkynyl, phenyl or aryl. In one embodiment, each of Q$_4$, Q$_5$, Q$_6$, Q$_1$, Q$_2$ and Q$_3$ is an independent substituent group; in another embodiment, at least two of Q$_4$, Q$_5$, Q$_6$, Q$_1$, Q$_2$ and Q$_3$ adjacent to each other joined into a ring.

In the above reaction equation (a) of step 1, alkalinity of Q$_4$Q$_5$Q$_6$N is stronger than that of Q$_1$Q$_2$Q$_3$N; or Q$_1$Q$_2$Q$_3$N is a volatile gas and Q$_4$Q$_5$Q$_6$N is a liquid or a solid whose boiling point is higher than that of Q$_1$Q$_2$Q$_3$N.

In the above reaction equation (b) of step 1, alkalinity of Q$_4$Q$_5$Q$_6$P is stronger than that of Q$_1$Q$_2$Q$_3$P; or Q$_1$Q$_2$Q$_3$P is a volatile gas and Q$_4$Q$_5$Q$_6$P is a liquid or a solid whose boiling point is higher than that of Q$_1$Q$_2$Q$_3$P.

In the above reaction equation (c) of step 1, alkalinity of Q$_4$Q$_5$Q$_6$N is stronger than that of Q$_1$Q$_2$Q$_3$P; or Q$_1$Q$_2$Q$_3$P is a volatile gas and Q$_4$Q$_5$Q$_6$N is a liquid or a solid whose boiling point is higher than that of Q$_1$Q$_2$Q$_3$P.

In the above reaction equation (d) of step 1, alkalinity of Q$_4$Q$_5$Q$_6$P is stronger than that of Q$_1$Q$_2$Q$_3$N; or Q$_1$Q$_2$Q$_3$N is a volatile gas and Q$_4$Q$_5$Q$_6$P is a liquid or a solid whose boiling point is higher than that of Q$_1$Q$_2$Q$_3$N.

There is no ion exchange and no water introduction involved in the preparation method of the present disclosure. The product ammonium salts or phosphonium salts yielded in the method have a content of halogen anions (Cl$^-$, Br$^-$, I$^-$) less than 10 ppm and a moisture content less than 50 ppm. The products prepared by the present disclosure can further act as a reactant to prepare other ammonium salts or phosphonium salts.

In one embodiment, the Q$_4$Q$_5$Q$_6$N is selected from at least one of the following: N-propylpyrrolidine, N-butylpyrrolidine, N-ethylpiperidine, N-propylpiperidine, N-butylpiperidine, triethylamine and dimethyloctylamine.

In another embodiment, the Q$_4$Q$_5$Q$_6$N is selected from at least one of the following: dipropylamine, dioctylamine, didecylamine and didodecylamine.

In yet another embodiment, the Q$_4$Q$_5$Q$_6$N is selected from at least one the following: n-hexylamine, ethanolamine, tetradecylamine and hexadecylamine.

In still another embodiment, the Q$_4$Q$_5$Q$_6$N is selected from at least one of the following: ethylimidazole, butylimidazole, pyridine and quinoline.

In another embodiment, the Q$_4$Q$_5$Q$_6$P is selected from at least one of the following: methylphosphine, dimethylphosphine, trimethylphosphine, ethylphosphine, diethylphosphine, triethylphosphine, tripropylphosphine, di-tert-butylphosphine, tri-tert-butylphosphine, tributylphosphine, tri-n-amyl phosphine, cyclohexyl phosphine, dicyclohexyl phosphine, tricyclohexyl phosphine, trihexylphosphine, trioctylphosphine, phenylphosphine, diphenylphosphine, triphenylphosphine, dimethylphenylphosphine, diethylphenylphosphine, diphenylbutylphosphine, tribenzylphosphine, trihydroxymethylphosphine, 2-chloroethane-diethylphosphine and tris(pentafluoroethyl)phosphine.

According to one embodiment of the present disclosure, a mole ratio of the reactants Q$_4$Q$_5$Q$_6$N to [Q$_1$Q$_2$Q$_3$NH]$^+$A$^-$, a mole ratio of the reactants Q$_4$Q$_5$Q$_6$P to [Q$_1$Q$_2$Q$_3$PH]$^+$A$^-$, a mole ratio of the reactants Q$_4$Q$_5$Q$_6$N to [Q$_1$Q$_2$Q$_3$PH]$^+$A$^-$, and a mole ratio of the reactants Q$_4$Q$_5$Q$_6$P to [Q$_1$Q$_2$Q$_3$NH]$^+$A$^-$, depend on the number of the protons included in the [Q$_1$Q$_2$Q$_3$NH]$^+$A$^-$ or [Q$_1$Q$_2$Q$_3$PH]$^+$A$^-$. In one embodiment, the Q$_4$Q$_5$Q$_6$N or Q$_4$Q$_5$Q$_6$P is properly excessive relative to [Q$_1$Q$_2$Q$_3$NH]$^+$A$^-$ or [Q$_1$Q$_2$Q$_3$PH]$^+$A$^-$. Taking the reaction of (C$_2$H$_5$)$_3$N and NH$_4$BF$_4$ as an example, the theoretical mole ratio thereof is 1:1. But as a salt, it is difficult for NH$_4$BF$_4$ to be removed by distillation or vacuum distillation. Accordingly, (C$_2$H$_5$)$_3$N is preferred to be properly excessive relative to NH$_4$BF$_4$. Taking the reaction of (C$_4$H$_9$)$_3$N and (NH$_4$)$_2$SO$_4$ as another example, the theoretical mole ratio thereof is 2:1, for the same reason as the above, (C$_4$H$_9$)$_3$N is properly excessive relative to (NH$_4$)$_2$SO$_4$. In general, the chosen of the reactants which can be properly excessive depends on the factors including material cost and difficult degree of waste recycling. In particular, environment-friendly reactants with low material cost are more inclined to be chosen as the properly excessive reactants.

According to one embodiment of the present disclosure, a mole ratio of the reactants [Q$_1$Q$_2$Q$_3$NH]$^+$A$^-$ to RCO$_3$R', or a mole ratio of the reactants [Q$_1$Q$_2$Q$_3$PH]$^+$A$^-$ to RCO$_3$R', depends on the number of the protons included in the $[Q_1Q_2Q_3NH]^+A^-$ or $[Q_1Q_2Q_3PH]^+A^-$. In one embodiment, the $RCO_3R'$ is properly excessive relative to $[Q_1Q_2Q_3NH]^+A^-$ or $[Q_1Q_2Q_3PH]^+A^-$.

Taking the reaction of $[(C_2H_5)_3NH]^+A^-$ and $(CH_3)_2CO_3$ as an example, the theoretical mole ratio thereof is 1:1. But as a salt, it is difficult for the $[(C_2H_5)_3NH]^+A^-$ to be removed by distillation or vacuum distillation. Accordingly, the $(CH_3)_2CO_3$ is properly excessive relative to $[(C_2H_5)_3NH]^+A^-$. Taking the reaction of $[(C_4H_9)_2NH_2]^+A^-$ and $(CH_3)_2CO_3$ as another example, the theoretical mole ratio thereof is 1:2, for the same reason as the above, the $RCO_3R'$ is properly excessive relative to $[(C_4H_9)_2NH_2]^+A^-$. In general, the chosen of the reactants which can be properly excessive depends on the factors including material cost and difficult degree of waste recycling. In particular, environment-friendly reactants with low material cost are more inclined to be chosen as the properly excessive reactants.

In one embodiment, in the reaction equation (a) of step 1, $Q_1Q_2Q_3N$ is selected from one of the following: an amine whose alkalinity is lower than that of $Q_4Q_5Q_6N$, a volatile amine, an ammonia whose alkalinity is lower than that of $Q_4Q_5Q_6N$, or a volatile ammonia; The anion $A^-$ is selected from at least one of the following: $PF_6^-$, $BF_4^-$, $SO_4^{2-}$, $NO_3^-$, $F^-$, $PO_4^{3-}$, $ClO_4^-$, $SiF_6^{2-}$, $(C_mF_{2m+1}SO_2)(C_nF_{2n+1}SO_2)N^-$, $(C_xF_{2x+1}SO_2)_2N^-$, $CF_3SO_3^-$, $CH_3CO_2^-$, $CF_3CO_2^-$, $C_3F_7CO_2^-$ and $(CN)_2N^-$, wherein m is an integer from 0 to 5, n is an integer from 0 to 5, x is an integer from 1 to 10.

In one embodiment, in the reaction equation (b) of step 1, $Q_1Q_2Q_3P$ is selected from one of the following: a phosphine whose alkalinity is lower than that of $Q_4Q_5Q_6P$, a volatile phosphine or hydrogen phosphide ($PH_3$). The anion $A-$ is selected from at least one of the following: $PF_6^-$, $BF_4^-$, $SO_4^{2-}$, $NO_3^-$, $F^-$, $PO_4^{3-}$, $ClO_4^-$, $SiF_6^{2-}$, $(C_mF_{2m+1}SO_2)(C_nF_{2n+1}SO_2)N^-$, $(C_xF_{2x+1}SO_2)_2N^-$, $CF_3SO_3^-$, $CH_3CO_2^-$, $CF_3CO_2^-$, $C_3F_7CO_2^-$ and $(CN)_2N^-$, wherein m is an integer from 0 to 5, n is an integer from 0 to 5, x is an integer from 1 to 10.

In one embodiment, in the reaction equation (c) of step 1, $Q_1Q_2Q_3P$ is selected from one of the following: a phosphine whose alkalinity is lower than that of $Q_4Q_5Q_6N$, a volatile phosphine or hydrogen phosphide ($PH_3$). The anion $A^-$ is selected from at least one of the following: $PF_6^-$, $BF_4^-$, $SO_4^{2-}$, $NO_3^-$, $F^-$, $PO_4^{3-}$, $ClO_4^-$, $SiF_6^{2-}$, $(C_mF_{2m+1}SO_2)(C_nF_{2n+1}SO_2)N^-$, $(C_xF_{2x+1}SO_2)_2N^-$, $CF_3SO_3^-$, $CH_3CO_2^-$, $CF_3CO_2^-$, $C_3F_7CO_2^-$ and $(CN)_2N^-$, wherein m is an integer from 0 to 5, n is an integer from 0 to 5, x is an integer from 1 to 10.

In one embodiment, in the reaction equation (d) of step 1, $Q_1Q_2Q_3N$ is selected from one of the following: an amine whose alkalinity is lower than that of $Q_4Q_5Q_6P$, a volatile amine, an ammonia whose alkalinity is lower than that of $Q_4Q_5Q_6P$, or a volatile ammonia. The anion $A^-$ is selected from at least one of the following: $PF_6^-$, $BF_4^-$, $SO_4^{2-}$, $NO_3^-$, $F^-$, $PO_4^{3-}$, $ClO_4^-$, $SiF_6^{2-}$, $(C_mF_{2m+1}SO_2)(C_nF_{2n+1}SO_2)N^-$, $(C_xF_{2x+1}SO_2)_2N^-$, $CF_3SO_3^-$, $CH_3CO_2^-$, $CF_3CO_2^-$, $C_3F_7CO_2^-$ and $(CN)_2N^-$, wherein m is an integer from 0 to 5, n is an integer from 0 to 5, x is an integer from 1 to 10.

In one embodiment, the $Q_1Q_2Q_3N$ is methylamine, dimethylamine, trimethylamine or ammonia ($NH_3$). The materials of $Q_1Q_2Q_3N$ above have the following advantages: first, since the alkalinity of methylamine, dimethylamine, trimethylamine and ammonia mentioned above is relatively weak, it is easy for them to be displaced by an amine whose alkalinity is stronger than theirs. Second, since they are gas under normal temperature and pressure, it is easy to obtain their dry product by various means. Third, since their boiling point is low, it is easy to separate them from other products or solvents by simple methods.

In one embodiment, a solvent is added into the reaction of step 1 and/or step 2. The solvent is selected from at least one of the following: alcohols, ethers, ketones, carbonates, nitriles, alkanes, halohydrocarbons and aromatic hydrocarbons. In another embodiment, the solvent is selected from at least one of the following: methanol, isopropanol, butanone and dimethyl-carbonate (DMC).

According to one embodiment of the present disclosure, the reaction is carried out in solvents. The usage of the solvent can facilitate the reactants to be mixed uniformly, and can also facilitate the reaction to be carried out in a lower temperature and get higher yield products. The selection of solvents depends on the physic-chemical characters of the reactants. Since amines or phosphines are easy to solve in various solvents, the selection of the solvent generally focuses on those that has certain solubility to $[Q_1Q_2Q_3N(P)H]^+A^-$ in order to prompt the reaction to complete. In general, methanol, isopropanol, butanone, dimethyl carbonate or the mixture thereof are selected as solvents.

In one embodiment, the reaction temperature of step 1 is controlled to be −20~100° C. In another embodiment, the reaction temperature of step 1 is 0~80° C. In still another embodiment, the reaction temperature of step 1 is 30~60° C.

In one embodiment, the absolute pressure of the reaction in step 1 is 0.05~2 Mpa. In another embodiment, the absolute pressure of the reaction in step 1 is 0.09~0.5 Mpa. In still another embodiment, the absolute pressure of the reaction in step 1 is 0.095~0.12 Mpa.

In one embodiment, the reaction time of step 1 is 0.1~72 hours. In another embodiment, the reaction time of step 1 is 6~36 hours. In still another embodiment, the reaction time of step 1 is 10~16 hours.

In one embodiment, the $RCO_3R'$ is selected from at least one of the following: dimethyl-carbonate, methyl ethyl carbonate (MEC), diethyl carbonate, ethylene carbonate, propylene carbonate (PC), methyl phenyl carbonate, diphenyl carbonate and dibenzyl carbonate. In another embodiment, the $RCO_3R'$ is selected from at least one of the following: dimethyl carbonate, methyl ethyl carbonate (MEC), diethyl carbonate and dibenzyl carbonate.

In one embodiment, the reaction temperature of step 2 is 90~280° C. In another embodiment, the reaction temperature of step 2 is 100~200° C. In still another embodiment, the reaction temperature of step 2 is 140~180° C.

In one embodiment, the absolute pressure of the reaction in step 2 is 0.1~3.0 Mpa. In another embodiment, the absolute pressure of the reaction in step 2 is 0.8~2.0 Mpa.

In one embodiment, the reaction time of step 2 is 0.1~12 hours. In another embodiment, the reaction time of step 2 is 0.5~8 hours. In still another embodiment, the reaction time of step 2 is 2~4 hours.

The present disclosure provides an ionic liquid, the content of halogen anions ($Cl^-$, $Br^-$, $I^-$) in the ionic liquid is less than 10 ppm, and the moisture content therein is less than 50 ppm. The present disclosure also provides a method for preparing the ionic liquid. The ionic liquid prepared by the method of the present disclosure is especially suitable for electrochemical systems which have high requirements to moisture content, such as lithium ion secondary batteries, and electrochemical supercapacitors, and also suitable for the application in the fields of green chemical industry, biology and catalysis.

DETAILED DESCRIPTION OF PREFERRED EMBODIMENTS

The present disclosure also provides an electrolyte used for secondary batteries, including the above mentioned ionic liquid.

The present disclosure also provides a lithium ion secondary battery, including the above mentioned electrolyte.

DETAILED DESCRIPTION OF PREFERRED EMBODIMENTS

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Embodiment 1

Previously, N-n-propyl pyrrole and anhydrous ammonium fluoride underwent a moisture removal treatment separately. After the moisture removal treatment, the content of the halogen anions ($Cl^-$, $Br^-$, $I^-$) in the N-n-propyl pyrrole is less than 5 ppm and moisture content thereof is less than 50 ppm; the content of the halogen anions ($Cl^-$, $Br^-$, $I^-$) in the anhydrous ammonium fluoride is less than 5 ppm and the moisture content thereof is less than 50 ppm. Next, under high purity nitrogen atmosphere, the treated N-n-propyl pyrrole (500 g, 4.42 mol) and anhydrous ammonium fluoride (4.41 mol) were added into a first reactor together, and 1000 mL mixed solvents of methanol and dimethyl carbonate were added into the first reactor. The content of halogen anions ($Cl^-$, $Br^-$, $I^-$) in the mixed solvents is less than 5 ppm and the moisture content thereof is less than 50 ppm. After addition, the mixture were reacted under 40° C. for 72 hours. After reaction, the liquid phase was transferred to a second reactor. Then, the temperature of the liquid phase was raised to 80° C. to distil out most solvents and unreacted reactants, and then the temperature was decreased to 60° C. to remove the low boiling point materials by vacuum distillation. Next, 1200 mL dimethyl carbonate was added into the second reactor under high purity nitrogen atmosphere, and reacted under 160° C. and 2.0 MPa for 8 hours, wherein the content of the halogen anions ($Cl^-$, $Br^-$, $I^-$) in the dimethyl carbonate is less than 5 ppm and the moisture content is less than 50 ppm. Some of the gas inside the reactor was released by the air evacuation valve to avoid excess pressure. After reaction, low boiling point materials were removed by vacuum distillation, and the reaction yielded N-methyl-N-propylpyrrolidine hydrofluoride (4.12 mol). According to the tests, the total content of $Cl^-$, $Br^-$ and $I^-$ in the product is less than 5 ppm and moisture content is less than 50 ppm.

Embodiment 2

Previously, N-n-propyl pyrrole and ammonium sulphate underwent a moisture removal treatment separately. After the treatment, the content of the halogen anions ($Cl^-$, $Br^-$, $I^-$) in the N-n-propyl pyrrole is less than 5 ppm and moisture content thereof is less than 50 ppm; and the content of the halogen anions ($Cl^-$, $Br^-$, $I^-$) in the ammonium sulphate is less than 5 ppm and the moisture content thereof is less than 50 ppm. Next, under high purity nitrogen atmosphere, the treated N-n-propyl pyrrole (500 g, 4.42 mol) and ammonium sulphate (2.00 mol) were added into a first reactor together, and 1500 mL anhydrous methanol was added into the first reactor. The content of halogen anions ($Cl^-$, $Br^-$, $I^-$) in the anhydrous methanol is less than 5 ppm and the moisture content thereof is less than 50 ppm. After addition, the temperature was raised to 68° C. and then the mixture reacted under condensing reflux for 24 hours. After reaction, the liquid phase was transferred to a second reactor. Then, the solvents and unreacted reactants were removed by distillation or vacuum distillation. Next, under high purity nitrogen atmosphere, 1000 mL dimethyl carbonate was added into the second reactor and reacted under 150° C. and 1.4 MPa for 6 hours, wherein the content of the halogen anions ($Cl^-$, $Br^-$, $I^-$) in the dimethyl carbonate is less than 5 ppm and the moisture content thereof is less than 50 ppm. Some of the gas inside the reactor was released by the air evaluation valve to avoid excess pressure. After reaction, low boiling point materials were removed by vacuum distillation. Further, the crude product was dried under nitrogen atmosphere to yield N-methyl-N-propylpyrrolidine sulphate (1.85 mol). According to the tests, the total content of $Cl^-$, $Br^-$ and $I^-$ in the final product is less than 4 ppm and the moisture content is less than 20 ppm.

Embodiment 3

Previously, tributylamine and trimethylammonium tetrafluoroborate underwent a moisture removal treatment separately. After the treatment, the content of the halogen anions ($Cl^-$, $Br^-$, $I^-$) in the tributylamine is less than 5 ppm and moisture content thereof is less than 50 ppm; the content of the halogen anions ($Cl^-$, $Br^-$, $I^-$) in the trimethylammonium tetrafluoroborate is less than 5 ppm and the moisture content thereof is less than 50 ppm. Next, under high purity nitrogen atmosphere, the treated tributylamine (500 g, 2.70 mol) and trimethylammonium tetrafluoroborate (2.69 mol) were added into a first reactor together, 800 mL anhydrous ethanol was added into the first reactor. The content of halogen anions ($Cl^-$, $Br^-$, $I^-$) in the anhydrous ethanol is less than 5 ppm and the moisture content thereof is less than 50 ppm. After addition, the mixture were reacted under 80° C. for 12 hours. After reaction, the liquid phase was transferred to a second reactor, solvents and unreacted reactants were removed by distillation or vacuum distillation. Next, under high purity nitrogen atmosphere, 1000 mL dimethyl carbonate was added into the second reactor and reacted under 160° C. and 1.5 MPa for 6 hours, wherein the content of the halogen anions ($Cl^-$, $Br^-$, $I^-$) in the dimethyl carbonate is less than 5 ppm and the moisture content is less than 50 ppm. Some of the gas inside the reactor was released by the air evacuation valve to avoid excess pressure. After the reaction, low boiling point materials were removed by vacuum distillation. Further, the crude product is dried under nitrogen atmosphere to yield methyltributylammonium tetrafluoroborate (2.55 mol). According to the tests, the total content of $Cl^-$, $Br^-$ and $I^-$ in the final product is less than 3 ppm and moisture content is less than 30 ppm.

Embodiment 4

Previously, N-n-butyl piperidine and bis(trifluoromethylsulfonyl)imide ammonium salt underwent a moisture removal treatment separately. After the moisture removal treatment, the content of the halogen anions ($Cl^-$, $Br^-$, $I^-$) in the N-n-butylpiperidine is less than 5 ppm and moisture content thereof is less than 50 ppm; and the content of the halogen anions ($Cl^-$, $Br^-$, $I^-$) in the bis(trifluoromethylsulfonyl)imide ammonium salt is less than 5 ppm and moisture content thereof is less than 50 ppm. Next, under high purity nitrogen atmosphere, the treated N-n-butylpiperidine (650 g, 4.61 mol) and bis(trifluoromethylsulfonyl)imide ammonia salt (4.60 mol) were added into a first reactor together, and 1500 mL anhydrous methanol was added into the first reactor. The content of halogen anions ($Cl^-$, $Br^-$, $I^-$) is less than 5 ppm and moisture content is less than 50 ppm. After addition, the temperature was raised to 60° C., and the mixture was reacted under 60° C. for 48 hours. After the reaction, the liquid phase was transferred to a second reactor, and then the solvents and unreacted reactants were removed by distillation or vacuum distillation. Next, 1000 mL dimethyl carbonate was added into the second reactor under high purity nitrogen atmosphere, and reacted under 160° C. and 1.6 MPa for 6 hours, wherein the content of the halogen anions ($Cl^-$, $Br^-$, $I^-$) in the dimethyl carbonate is less than 5 ppm and the moisture content thereof is less than 50 ppm. Some of the gas inside the reactor was released by the air evaluation valve to avoid excess pressure. After reaction, low boiling point materials were removed by vacuum distillation. Further, the crude product was dried under nitrogen atmosphere to yield N-methyl-N-butylpiperidine bis(trifluoromethylsulfonyl)imide (4.22 mol). According to the tests, the total content of $Cl^-$, $Br^-$ and $I^-$ in the product is less than 3 ppm and the moisture content thereof is less than 40 ppm.

Embodiment 5

Previously, triethylphosphine and bis(trifluoromethylsulfonyl)imide phosphonium salt underwent a moisture removal treatment separately. After the treatment, the content of the halogen anions ($Cl^-$, $Br^-$, $I^-$) in the triethylphosphine is less than 5 ppm and moisture content thereof is less than 50 ppm; and the content of the halogen anions ($Cl^-$, $Br^-$, $I^-$) in the bis(trifluoromethylsulfonyl)imide phosphonium salt is less than 5 ppm and moisture content thereof is less than 50 ppm. Next, under high purity nitrogen atmosphere, the treated triethylphosphine (300 g, 2.54 mol), treated bis(trifluoromethylsulfonyl)imide phosphonium salt (2.53 mol), and 1000 mL anhydrous methanol were added into a first reactor together. The content of the halogen anions ($Cl^-$, $Br^-$, $I^-$) in the anhydrous methanol is less than 5 ppm and moisture content thereof is less than 50 ppm. Then the temperature was raised to 60° C. and the reaction continued for 3 hours at 60° C. After the reaction, liquid phase was transferred to a second reactor, and the solvents and unreacted reactants were removed by distillation or vacuum distillation. Next, 900 mL diethylcarbonate was added into the second reactor under high purity nitrogen atmosphere, and reacted under 180° C. and 1.8 MPa for 12 hours, wherein the content of halogen anions ($Cl^-$, $Br^-$, $I^-$) is less than 5 ppm and moisture content thereof is less than 50 ppm. Some of the gas inside the reactor was released by the air evacuation valve to avoid excess pressure. After reaction, low boiling point materials were removed by vacuum distillation to yield a crude product. Further, the crude product was dried under nitrogen atmosphere to yield tetraethyl quaternary phosphonium bis(trifluoromethylsulfonyl)imide (1.20 mol). According to the tests, the total content of $Cl^-$, $Br^-$ and $I^-$ in the product is less than 5 ppm and the moisture content thereof is less than 50 ppm.

Embodiment 6

Previously, N-n-propyl pyrrole and bis(fluorosulfonyl)imide phosphonium salt underwent a moisture removal treatment separately. After the treatment, the content of the halogen anions ($Cl^-$, $Br^-$, $I^-$) in the N-n-propyl pyrrole is less than 5 ppm and moisture content thereof is less than 50 ppm; and the content of halogen anions ($Cl^-$, $Br^-$, $I^-$) in the bis(fluorosulfonyl)imide phosphonium salt is less than 5 ppm and the moisture content thereof is less than 50 ppm. Next, under high purity nitrogen atmosphere, the treated N-n-propyl pyrrole (500 g, 4.42 mol) and the treated bis (fluorosulfonyl)imide phosphonium salt (4.41 mol), together with 1200 mL treated dimethyl carbonate were added into a first reactor. The content of halogen anions ($Cl^-$, $Br^-$, $I^-$) in the dimethyl carbonate is less than 5 ppm and the moisture content thereof is less than 50 ppm. Mixing them uniformly and raising temperature to 80° C., the reaction took place at 80° C. for 24 hours. After the reaction, liquid phase was transferred to a second reactor, solvents and unreacted reactants were removed by distillation or vacuum distillation. Next, 900 mL dimethyl carbonate was further added into the second reactor, and then reacted at 160° C. and 1.8 MPa for 5 hours, wherein the content of halogen anions ($Cl^-$, $Br^-$, $I^-$) is less than 5 ppm and moisture content thereof is less than 50 ppm. Some of the gas inside the reactor was released by the air evacuation valve to avoid excess pressure. After reaction, low boiling point materials were removed by vacuum distillation to yield a crude product. The crude product was further dried under nitrogen atmosphere to yield N-methyl-N-propylpyrrolidinium bis(trifluoromethylsulfonyl)imide (4.00 mol). According to the tests, the total content of $Cl^-$, $Br^-$ and $I^-$ in the product is less than 4 ppm and moisture content is less than 50 ppm.

Embodiment 7

Under high purity nitrogen atmosphere, N,N-dimethyl octylamine (400 g, 2.55 mol) and bis(trifluoromethylsulfonyl)imide (2.55 mol) were added into a first reactor, together with 1000 mL anhydrous methanol. In N,N-dimethyl octylamine, the content of halogen anions ($Cl^-$, $Br^-$, $I^-$) is less than 5 ppm and moisture content is less than 50 ppm; In bis(trifluoromethylsulfonyl)imide, the content of halogen anions ($Cl^-$, $Br^-$, $I^-$) is less than 5 ppm and moisture content is less than 50 ppm; In anhydrous methanol, the content of halogen anions ($Cl^-$, $Br^-$, $I^-$) is less than 5 ppm and moisture content is less than 50 ppm. Next, mixed them to be uniform, and the temperature was raised to 60° C., the reaction continued at 60° C. for 36 hours. After the reaction, liquid phase was transferred to a second reactor, solvents and unreacted reactants were removed by distillation or vacuum distillation. Then, 1200 mL dimethyl carbonate was further added into the second reactor under high purity nitrogen atmosphere, and then reacted at 160° C. and 1.7 MPa for 8 hours, wherein the content of halogen anions ($Cl^-$, $Br^-$, $I^-$) is less than 5 ppm and moisture content is less than 50 ppm. Some of the gas inside the reactor was released by the air evacuation valve to avoid excess pressure. After reaction, low boiling point materials were removed by vacuum distillation to yield a crude product. The crude product was further dried under nitrogen atmosphere to yield N,N,N-trimethyl octyl ammonium bis(trifluoromethylsulfonyl)imide (2.24 mol). According to the tests, the total content of $Cl^-$, $Br^-$, $I^-$ in the final product is less than 5 ppm and the moisture content is less than 50 ppm.

Embodiment 8

N-n-butyl piperidine (480 g, 3.40 mol) and phosphonium fluoride (3.38 mol) were added into a first reactor and mixed to be uniform under high purity nitrogen atmosphere, wherein the content of halogen anions ($Cl^-$, $Br^-$, $I^-$) in N-n-butyl piperidine is less than 5 ppm and moisture content therein is less than 50 ppm; the content of halogen anions ($Cl^-$, $Br^-$, $I^-$) in phosphonium fluoride is less than 5 ppm and moisture content therein is less than 50 ppm. Raising the temperature to 95° C. and reacting for 0.1 hours, and then decreasing the temperature to 80° C. and removing gas by decompression. Next, 900 mL dimethyl carbonate was further added into the reactor under high purity nitrogen atmosphere, wherein the content of halogen anions ($Cl^-$, $Br^-$, $I^-$) is less than 5 ppm and the moisture content is less than 50 ppm. Reacting at 160° C. and 1.8 MPa for 5 hours. Some of the gas inside the reactor was released by the air evacuation valve to avoid excess pressure. After reaction, low boiling point materials were removed by vacuum distillation to yield a crude product. The crude product was further dried under nitrogen atmosphere to yield N-methyl-N-butyl piperidinium hydrofluoride (2.68 mol). According to the tests, the total content of $Cl^-$, $Br^-$, $I^-$ in the product is less than 5 ppm and moisture content is less than 40 ppm.

Embodiment 9

N-ethyl pyrrolidine (450 g, 4.55 mol) and phosphonium fluoride (4.52 mol) were added into a first reactor under high purity nitrogen atmosphere, and mixed to be uniform at −20° C. and reacted for 5 hours, wherein the content of halogen anions ($Cl^-$, $Br^-$, $I^-$) in N-ethyl pyrrolidine is less than 5 ppm and moisture content therein is less than 50 ppm; and the content of halogen anions ($Cl^-$, $Br^-$, $I^-$) in phosphonium fluoride is less than 5 ppm and moisture content therein is less than 50 ppm. Removing gas by decompression, 1000 mL dimethyl carbonate was further added into the reactor under high purity nitrogen atmosphere, wherein the content of halogen anions ($Cl^-$, $Br^-$, $I^-$) is less than 5 ppm and moisture content is less than 50 ppm. After addition, reacting at 90° C. and 2.4 MPa for 36 hours. Some of the gas inside the reactor was released by the air evacuation valve to avoid excess pressure. After reaction, low boiling point materials were removed by vacuum distillation to yield a crude product. The crude product was further dried under nitrogen atmosphere to yield N-methyl-N-ethyl pyrrolidinium hydrofluoride (3.42 mol). According to the tests, the total content of $Cl^-$, $Br^-$, $I^-$ in the product is less than 3 ppm and the moisture content is less than 40 ppm.

It will be understood that the above particular embodiments are shown and described by way of illustration only. The principles and the features of the present disclosure may be employed in various and numerous embodiments thereof without departing from the scope of the disclosure. The above-described embodiments illustrate the scope of the disclosure but do not restrict the scope of the disclosure.

What is claimed is:

1. A preparation method of an ionic liquid, wherein a total content of halogen anions in the ionic liquid is less than 10 ppm, and moisture content in the ionic liquid is less than 50 ppm; the halogen anions are $Cl^-$, $Br^-$ and $I^-$, comprising the following steps:

Step 1: preparing an ammonium salt or a phosphonium salt, reaction equations as below:

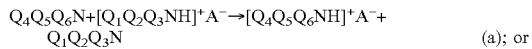

(a); or

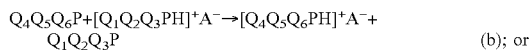

(b); or

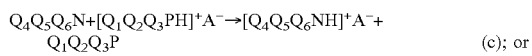

(c); or

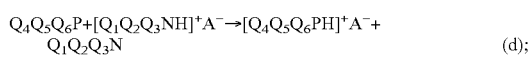

(d);

Step 2: the ammonium salt or the phosphonium salt prepared in step 1 reacts with a carbonate ester to produce a quaternary ammonium salt or a quaternary phosphonium salt, reaction equations as below:

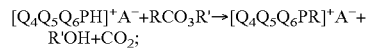

wherein each of $Q_4$, $Q_5$, $Q_6$, $Q_1$, $Q_2$ and $Q_3$ is selected from hydrogen, alkyl, alkenyl, alkynyl, phenyl or aryl; or each of $Q_4$, $Q_5$, $Q_6$, $Q_1$, $Q_2$ and $Q_3$ is an organic group comprising at least one element selected from boron, silicon, nitrogen, phosphorus, oxygen, sulfur, fluorine, chlorine, bromine and iodine; said organic group is alkyl, alkenyl, alkynyl, phenyl or aryl; wherein each of said $Q_4$, $Q_5$, $Q_6$, $Q_1$, $Q_2$ and $Q_3$ is an independent substituent group; or at least two of said $Q_4$, $Q_5$, $Q_6$, $Q_1$, $Q_2$ and $Q_3$ adjacent to each other joint into a ring;

wherein each of said R and R' is selected from alkyl, alkenyl, alkynyl, phenyl or aryl; or each of said R and R' is a group comprising at least one element selected from boron, silicon, nitrogen, phosphorus, oxygen, sulfur, fluorine, chlorine, bromine and iodine; wherein each of said R and R' is an independent substituent group or R and R' adjacent to each other joint into a ring;

in reaction equation (a) of step 1, alkalinity of the $Q_4Q_5Q_6N$ is stronger than that of $Q_1Q_2Q_3N$; or $Q_1Q_2Q_3N$ is a volatile gas and $Q_4Q_5Q_6N$ is a liquid or a solid whose boiling point is higher than that of $Q_1Q_2Q_3N$;

in reaction equation (b) of step 1, alkalinity of the $Q_4Q_5Q_6P$ is stronger than that of $Q_1Q_2Q_3P$; or $Q_1Q_2Q_3P$ is a volatile gas and $Q_4Q_5Q_6P$ is a liquid or a solid whose boiling point is higher than that of $Q_1Q_2Q_3P$;

in reaction equation (c) of step 1, alkalinity of the $Q_4Q_5Q_6N$ is stronger than that of $Q_1Q_2Q_3P$; or $Q_1Q_2Q_3P$ is a volatile gas and $Q_4Q_5Q_6N$ is a liquid or a solid whose boiling point is higher than that of $Q_1Q_2Q_3P$;

in reaction equation (d) of step 1, alkalinity of the $Q_4Q_5Q_6P$ is stronger than that of $Q_1Q_2Q_3N$; or $Q_1Q_2Q_3N$ is a volatile gas and $Q_4Q_5Q_6P$ is a liquid or a solid whose boiling point is higher than that of $Q_1Q_2Q_3N$.

2. The preparation method of the ionic liquid of claim 1, wherein said $Q_4Q_5Q_6N$ is at least one selected from the group consisting of N-propylpyrrolidine, N-butylpyrrolidine, N-ethylpiperidine, N-propylpiperidine, N-butylpiperidine, triethylamine and dimethyloctylamine.

3. The preparation method of the ionic liquid of claim 1, wherein said $Q_4Q_5Q_6N$ is at least one selected from dipropylamine, dioctyl amine, didecylamine and didodecylamine.

4. The preparation method of the ionic liquid of claim 1, wherein said $Q_4Q_5Q_6N$ is at least one selected from n-hexylamine, ethanolamine, tetradecylamine and hexadecylamine.

5. The preparation method of the ionic liquid of claim 1, wherein said $Q_4Q_5Q_6N$ is at least one selected from ethylimidazole, butylimidazole, pyridine and quinoline.

6. The preparation method of the ionic liquid of claim 1, wherein said $Q_4Q_5Q_6P$ is at least one selected from methylphosphine, dimethylphosphine, trimethylphosphine, ethylphosphine, diethylphosphine, triethylphosphine, tripropylphosphine, di-butylphosphine, tri-tert-butylphosphine, tributylphosphine, tri-n-amyl phosphine, cyclohexyl phosphine, dicyclohexyl phosphine, tricyclohexyl phosphine, trihexylphosphine, trioctylphosphine, phenylphosphine, diphenylphosphine, triphenylphosphine, dimethylphenylphosphine, diethylphenylphosphine, diphenylbutylphosphine, tribenzylphosphine, trihydroxymethylphosphine, 2-chloroethanediethylphosphine and tris(pentafluoroethyl) phosphine.

7. The preparation method of the ionic liquid of claim 1, wherein in reaction equation (a) of step 1, $Q_1Q_2Q_3N$ is selected from one of the following: an amine whose alkalinity is lower than that of $Q_4Q_5Q_6N$, a volatile amine, an ammonia whose alkalinity is lower than that of $Q_4Q_5Q_6N$, and a volatile ammonia; the anion $A^-$ is selected from at least one of the following: $PF_6^-$, $BF_4^-$, $SO_4^{2-}$, $NO_3^-$, $F^-$, $PO_4^{3-}$, $ClO_4^-$, $SiF_6^{2-}$, $(C_mF_{2m+1}SO_2)(C_nF_{2n+1}SO_2)N^-$, $(C_xF_{2x+1}SO_2)_2N^-$, $CF_3SO_3^-$, $CH_3CO_2^-$, $CF_3CO_2^-$, $C_3F_7CO_2^-$ and $(CN)_2N^-$, wherein m is an integer from 0 to 5, n is an integer from 0 to 5, x is an integer from 1 to 10.

8. The preparation method of the ionic liquid of claim 1, wherein in reaction equation (b) of step 1, $Q_1Q_2Q_3P$ is selected from one of the following: a phosphine whose alkalinity is lower than that of $Q_4Q_5Q_6P$, a volatile phosphine or hydrogen phosphide; the anion A- is selected from at least one of the following: $PF_6^-$, $BF_4^-$, $SO_4^{2-}$, $NO_3^-$, $F^-$, $PO_4^{3-}$, $ClO_4^-$, $SiF_6^{2-}$, $(C_mF_{2m+1}SO_2)(C_nF_{2n+1}SO_2)N^-$, $(C_xF_{2x+1}SO_2)_2N^-$, $CF_3SO_3$, $CH_3CO_2^-$, $CF_3CO_2^-$, $C_3F_7CO_2^-$ and $(CN)_2N^-$; wherein m is an integer from 0 to 5, n is an integer from 0 to 5, x is an integer from 1 to 10.

9. The preparation method of the ionic liquid of claim 1, wherein in reaction equation (c) of step 1, $Q_1Q_2Q_3P$ is selected from one of the following: a phosphine whose alkalinity is lower than that of $Q_4Q_5Q_6N$, a volatile phosphine or hydrogen phosphide, the anion $A^-$ is selected from at least one of the following: $PF_6^-$, $BF_4^-$, $SO_4^{2-}$, $NO_3^-$, $F^-$, $PO_4^{3-}$, $ClO_4^-$, $SiF_6^{2-}$, $(C_mF_{2m+1}SO_2)(C_nF_{2n+1}SO_2)N^-$, $(C_xF_{2x+1}SO_2)_2N^-$, $CF_3SO_3^-$, $CH_3CO_2^-$, $CF_3CO_2^-$, $C_3F_7CO_2^-$ and $(CN)_2N^-$, wherein m is an integer from 0 to 5, n is an integer from 0 to 5, x is an integer from 1 to 10.

10. The preparation method of the ionic liquid of claim 1, wherein in reaction equation (d) of step 1, $Q_1Q_2Q_3N$ is selected from one of the following: an amine whose alkalinity is lower than that of $Q_4Q_5Q_6P$, a volatile amine, an ammonia whose alkalinity is lower than that of $Q_4Q_5Q_6P$ and a volatile ammonia; the anion $A^-$ is selected from at least one of the following: $PF_6^-$, $BF_4^-$, $SO_4^{2-}$, $NO_3^-$, $F^-$, $PO_4^{3-}$, $ClO_4^-$, $SiF_6^{2-}$, $(C_mF_{2m+1}SO_2)(C_nF_{2n+1}SO_2)N^-$, $(C_xF_{2x+1}SO_2)_2N^-$, $CF_3SO_3^-$, $CH_3CO_2^-$, $CF_3CO_2^-$, $C_3F_7CO_2^-$ and $(CN)_2N^-$, wherein m is an integer from 0 to 5, n is an integer from 0 to 5, x is an integer from 1 to 10.

11. The preparation method of the ionic liquid of claim 7, wherein said $Q_1Q_2Q_3N$ is selected from methylamine, dimethylamine, trimethylamine or ammonia.

12. The preparation method of the ionic liquid of claim 10, wherein said $Q_1Q_2Q_3N$ is selected from methylamine, dimethylamine, trimethylamine or ammonia.

13. The preparation method of the ionic liquid of claim 1, wherein a solvent is added into the reaction of step 1 and/or step 2; the solvent is selected from at least one of the following: alcohols, ethers, ketones, carbonates, nitriles, alkanes, halohydrocarbons and aromatic hydrocarbons.

14. The preparation method of the ionic liquid of claim 13, wherein the solvent is selected from at least one of the following: methanol, isopropanol, butanone and dimethyl carbonate.

15. The preparation method of the ionic liquid of claim 1, wherein the reaction temperature of step 1 is from −20 to 100° C.

16. The preparation method of the ionic liquid of claim 1, wherein the absolute pressure of the reaction in step 1 is from 0.05 to 2 MPa.

17. The preparation method of the ionic liquid of claim 1, wherein the reaction time of step 1 is from 0.1 to 72 hours.

18. The preparation method of the ionic liquid of claim 1, wherein said $RCO_3R'$ is selected from at least one of the following: dimethyl carbonate, methyl ethyl carbonate, diethyl carbonate, ethylene carbonate, propylene carbonate, methyl phenyl carbonate, diphenyl carbonate and dibenzyl carbonate.

19. The preparation method of the ionic liquid of claim 1, wherein the reaction temperature of step 2 is from 60 to 280° C.

20. The preparation method of the ionic liquid of claim 1, wherein the absolute pressure of the reaction in step 2 is from 0.1 MPa to 3.0 MPa.

21. The preparation method of the ionic liquid of claim 1, wherein the reaction time of step 2 is from 0.1 to 12 hours.

22. The preparation method of the ionic liquid of claim 1, wherein said $Q_4Q_5Q_6N$ is tributylamine.

* * * * *